United States Patent [19]
Todoroki et al.

[11] Patent Number: 5,699,163
[45] Date of Patent: Dec. 16, 1997

[54] METHOD OF DETERMINING THE ORIENTATION OF FIBERS ON THE SURFACE OF PAPER

[75] Inventors: Hidenobu Todoroki; Yuji Abe; Akira Sakamoto; Nobuo Takeuchi, all of Tokyo, Japan

[73] Assignee: Nippon Paper Industries Co., Ltd., Tokyo, Japan

[21] Appl. No.: 549,806

[22] PCT Filed: Apr. 6, 1995

[86] PCT No.: PCT/JP95/00668

§ 371 Date: Dec. 6, 1995

§ 102(e) Date: Dec. 6, 1995

[87] PCT Pub. No.: WO95/27893

PCT Pub. Date: Oct. 19, 1995

[30] Foreign Application Priority Data

Apr. 6, 1994 [JP] Japan .................................. 6-090727

[51] Int. Cl.$^6$ .............................. G01N 21/55; G01J 4/00
[52] U.S. Cl. ............................................ 356/445; 356/369
[58] Field of Search ................................. 356/369, 445

[56] References Cited

U.S. PATENT DOCUMENTS

| | | | |
|---|---|---|---|
| 3,807,868 | 4/1974 | Simila | 356/369 |
| 5,317,387 | 5/1994 | Van Hengel et al. | 356/372 |

FOREIGN PATENT DOCUMENTS

| | | |
|---|---|---|
| 4113205 | 9/1990 | Japan . |
| 4-95845 | 3/1992 | Japan . |
| 4-127004 | 4/1992 | Japan . |
| 5-40259 | 6/1993 | Japan . |
| 6-257092 | 9/1994 | Japan . |
| 7-229831 | 8/1995 | Japan . |

OTHER PUBLICATIONS

Journal of Pulp and Paper Technology Association, vol. 48, No. 3, pp. 456–460, Mar. 3, 1994, Kiyokazu Sakai, et al., "On-Line Fiber Orientation Measuring System for Papers" (with partial English translation.

International Paper Physics Conference Book 1, pp. 81–87, 1991, Pierre Bernard, et al., "Probing Fiber Orientation Distribution Via Ellipsometric Measurements in the Far Infrared" (no month available).

*Primary Examiner*—Frank G. Font
*Assistant Examiner*—Amanda Merlino
*Attorney, Agent, or Firm*—Oblon, Spivak, McCleland, Maier & Neustadt, P.C.

[57] ABSTRACT

A method of determining the orientation of fibers on the surface of paper rather than measuring the orientation of fibers throughout the entire layer of paper is provided. In directing incident light Li from a projecting unit 6 to the surface 1a of the paper 1 to be measured at a given angle (θi) of incidence and receiving by a receiving unit 7 the intensity of light reflected Lo by and off the surface 1a of the paper 1 at the same angle (θo) of regular reflection as the angle (θi) of incidence, the incident light Li containing at least the linearly polarized principal ray is allowed to be incident on the surface 1a of the paper 1, so that at least the linearly polarized principal ray can be received by the receiving unit 7 in the form of reflected light Lo, and the surface 1a of the paper 1 is inclined at an angle (α) of inclination around the line of intersection of a plane M of incidence and reflection through which the incident light Li and reflected light Lo pass with the surface 1a of the paper 1 while the paper 1 is rotated relative to the plane of incidence and reflection around the center axis of rotation defined by a line that passes through a center point 3 of the surface 1a of the paper 1 irradiated with the incident light and is vertical to the surface of the paper, whereby the fiber orientation on the surface 1a of the paper 1 can be found from the intensity of the reflected light Lo received by the receiving unit 7 corresponding to the angle of rotation of the paper 1.

14 Claims, 2 Drawing Sheets

METHOD OF DETERMINING THE ORIENTATION OF FIBERS ON THE SURFACE OF PAPER

TECHNICAL FIELD

The present invention relates to a method of determining the orientation of fibers on the surface of a variety of paper such as PPC paper used with copiers, continuous form paper used with line printers for computers, etc., and paper material of which coated paper for posters is made.

BACKGROUND TECHNIQUE

As a measure of determining the properties of finished paper, the orientation of fibers has so far been widely used.

This fiber orientation of paper is generally represented by the angle of fiber orientation of paper and the intensity of orientation of paper fibers. By the former is meant the average direction in which fibers are arranged side by side, (viz., the direction in which the maximum number of fibers are arranged side by side). Here assume that the lengthy direction of a paper machine is zero degree. Then, the clockwise direction toward the downstream side of the paper machine is represented by the orientation angle of a plus (+) sign and the counterclockwise direction by the orientation angle of a (−) minus sign. By the latter is meant the ratio of the number of fibers arranged in the direction at right angles with the thus represented orientation angle of fibers (in which direction the minimum number of fibers are usually arranged) and the number of fibers arranged at that orientation angle of fibers. (This ratio is called the orientation ratio).

Such fiber orientation of paper correlates closely with paper strength or paper defects such as curling, warping or twisting etc. For example, this has close relations to PPC characteristics (the ability of cut paper sheets of small size to be received in the tray of a plain paper copy machine before copying or the ability of such sheets to be stacked one upon another or sorted after copying), running stability on fast printers or processors which becomes worse when paper sheets are fed in zigzag or other irregular ways, NIP characteristics (the ability of continuous form paper sheets used with a non-impact printer to be stacked one upon another after printing), etc.

Typically, the fiber orientation of paper has often been determined by obtaining test specimens at various angles with respect to the lengthy direction of a paper machine and measuring their tensile strengths at various angles with respect to the lengthy direction of a paper machine by tensile testing. With this method, however, much time is needed for obtaining data because the operation to obtain a number of test specimens is required and also tensile testings are needed as many as such specimens. In other words, a grave problem with this method is that data about the fiber orientation of paper measured cannot be fed back to meet the paper of the desired properties within an acceptably short time by adjusting the paper-making or processing conditions.

For eliminating such a problem and so measuring the fiber orientation of paper within a relatively short time, an apparatus—called a molecular orientation analyzer (available under the trade name of MOA-2001 manufactured by Kanzaki Seishi Co., Ltd.) is proposed and practically used so as to direct linearly polarized microwaves vertically to the paper sheet to be measured, thereby finding the fiber orientation of the sheet from the amount of attenuation of the output obtained through the sheet, as disclosed in Japanese Laid-Open Patent No. 60-227156. Another apparatus for determining the fiber orientation of a sheet from the angle distribution of the speed of propagation of ultrasonic waves, for instance, an apparatus available under the trade name of (SST-3000 manufactured by Nomura Shoji Co., Ltd.), is proposed and put to practical use.

However, none of the above-mentioned apparatus for determining the fiber orientation of paper within a relatively short time can be used for the purpose of determining the orientation of fibers present on the paper surface alone, because they are designed to use a medium transmitting through the paper to find the orientation of fibers throughout the entire layer of the paper in the form of an average value.

DISCLOSURE OF THE INVENTION

The inventors have made studies of commercially available paper sheets, and has consequently found that, in the case of paper sheets made by a fourdrinier paper machine that is most widely used for paper production, their fiber orientation is relatively stable on the wire side but varies largely on the opposite side. Such a fiber orientation difference between the two sides of paper represents an elongation difference between the two sides of paper, which is caused by changes in the moisture and temperature of paper that is, it is a great factor responsible for paper defects such as curling, warping and twisting.

It is therefore an object of the present invention to provide a method by which only the fiber orientation of the surface of paper can easily and readily be determined within a relatively short time rather than a method of measuring the fiber orientation of paper throughout its entire layer in an average value.

As a result of intensive studies made by the inventors to achieve the above-mentioned object, it has now been found that the fiber orientation of paper implies whether or not cellulose fibers that are elongate rod-like members forming the paper are in alignment with the lengthy direction of a paper machine. For instance, that cellulose fibers are in complete alignment with the lengthy direction of a paper machine at a given angle is believed to be tantamount to that a number of rod-like members are stacked one upon another at the same lengthy direction. Now consider the case where projecting and receiving units are arranged such that the projecting unit allows light to be incident on the surface of the paper—the fiber orientation of which is to be measured—at a given angle and the receiving unit receives the intensity of the light reflected by and off the surface of the paper at the same angle of regular reflection. The more the number of fibers arranged in the same direction as that in which the incident light strikes on a certain area of the surface of the paper irradiated, the higher the intensity of the light regularly reflected by the surfaces of the fibers and received by the receiving unit, and the less the number of fibers arranged in the same direction as that in which the incident light strikes on a certain area of the surface of the paper irradiated, the lower the intensity of the light regularly reflected by the surfaces of the fibers and received by the receiving unit. Furthermore in this case, any medium that can transmit through the paper to be measured is not used. Therefore, use of the incidence and reflection of light may provide one possible approach to determining the fiber orientation on the surface of paper.

Even in this arrangement where the projecting unit directs the incident light to the surface of the paper at a given angle of incidence and the receiving unit receives the reflected light, however, the light received by the receiving unit contains not only the light resulting from the reflection of the incident light from the surface of the paper but also the light introduced by the incident light passing through and intra-layer diffused ray in the layer of the paper and then coming back to the surface side of the paper. For instance, when the fibers are in a rectangular column form with the planes being parallel with the surface of the paper, the reflected light also contains light reflected from the surfaces of the fibers. This is true of even when the direction of orientation of the fibers are in no alignment with the direction of the optic axis in which the incident light from the projecting unit is directed to the surface of the paper. Thus some considerable errors arise from both the reflected light and the intra-layer diffused ray contained in the light received by the receiving unit, and then detract much from data reliability. Especially when the fiber orientation of paper is expressed in terms of the intensity of fiber orientation, those errors are of serious significance.

Then, the inventors have made extensive studies of why such errors arise in order to dissolve the cause thereof. As mentioned just above, error arises from the fact that the reflected light contains components reflected from the surfaces of fibers with the orientation direction being in no alignment with the direction of the optic axis in which the incident light from the projecting unit is directed to the surface of the paper. Here consider the case where the surface of the paper to be measured forms a plane at an angle with respect to the plane of incidence and reflection through which the incident light and reflected light pass, that is, the surface of the paper to be measured is inclined at a given angle around the line of intersection of the plane of incident and reflection through which the incident light and reflected light pass with the surface of the paper to be measured, rather than the case where the plane of incidence and reflection through which the incident light and reflected light pass and the surface of the paper to be measured form a plane in which they are perpendicular to each other, as designed in conventional optical systems. In this case, when the fibers have their planes arranged parallel with the surface of the paper and orient in a direction that is in no alignment with the direction of the optic axis in which the incident light from the projecting unit is directed to the surface of the paper, the plane of incidence and reflection through which the incident light and reflected light pass does not contain any component reflected from the surfaces of the fibers. In other words, only ray of lights reflected from the sides of fibers lying parallel with the line of intersection of the plane of incidence and reflection through which the incident light and reflected light pass with the surface of the paper are received by the receiving unit in the form of reflected light. Thus the first error can be eliminated.

Error arises also from the fact that the diffused light is contained in the light received by the receiving unit. Paper-forming cellulose fibers are transparent or semi-transparent and so are considered to be much the same as glass fibers. Thus, if the incident light directed from the projecting unit to the surface of the paper at a given angle of incidence is polarized by a polarizer such as a polarizing filter into a linearly polarized ray having an oscillation plane in the vertical direction to the plane of incidence and reflection through which the incident light and reflected light pass, which has the highest reflectance factor with respect to the surface of a glass or other sheet, (hereinafter be called the linearly polarized principal ray), or if rays of lights containing the linearly polarized principal ray are directed to the surface of the paper without recourse to any polarizer, at least the linearly polarized principal ray alone can then be received by the polarizing unit, such error can be eliminated.

Thus, the present invention provides a method of determining the fiber orientation on the surface of paper by directing incident light from a projecting unit to the surface of the paper to be measured at a given angle of incidence, and receiving by a receiving unit the intensity of light reflected by and off the surface of the paper at the same angle of regular reflection as the angle of wherein:

the incident light containing at least the linearly polarized principal ray is allowed to be incident on the surface of the paper, so that at least the linearly polarized principal ray alone can be received by the receiving unit in the form of reflected light, and the surface of the paper is inclined at an angle of inclination around the line of intersection of a plane of incidence and reflection through which the incident light and reflected light pass with the surface of the paper while the paper is rotated relative to the plane of incidence and reflection around the center axis of rotation defined by a line that passes through a center point of the surface of the paper irradiated with the incident light and is vertical to the surface of the paper, whereby the fiber orientation on the surface of the paper can be found from the intensity of the reflected light received by the receiving unit corresponding to the angle of rotation of the paper. Thus, the present invention is accomplished.

BRIEF DESCRIPTION OF THE DRAWINGS

The method of determining the fiber orientation on the surface of paper according to the present invention will now be explained at great length with reference to the accompanying drawings, in which.

BEST MODE FOR CARRYING OUT THE INVENTION

Figure 1:
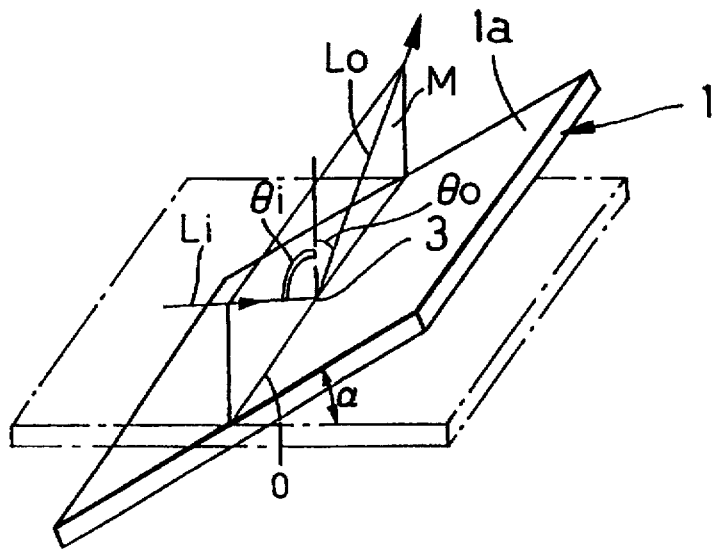
FIG. 1 is a perspective view of the present method which illustrates what relations are amongst the angle of incidence of incident light, the angle of regular reflection of the reflected light, and the angle of inclination of the surface of paper with respect to a plane of incidence and reflection through which the incident light and reflected light pass.

To practice the presently invented method in a laboratory or the like, there is provided a sample table 2 including a flat surface 2a on which is supported a paper sample 1 the surface of which is to be measured for its fiber orientation. This table 2 is provided with a drive 4 rotatable around a line that passes through a center point 3 (to be described later) to be irradiated with light and is vertical with respect to the flat surface 2a. There is also provided a rotary encoder 5 for detecting the angle ($\theta$) of rotation of the sample table 2 by the drive 4.

Moreover, a projecting unit 6 and a receiving unit 7 are located in a predetermined arrangement, said projecting unit 6 being designed such that incident light Li is projected at a given angle ($\theta i$) of incidence to the surface 1a of the paper 1 held on the support surface 2a of the table 2 and said receiving unit 7 being designed to receive and detect the intensity of reflected light Lo obtained by the reflection from the surface 1a of the paper 1 of the incident light Li coming from the projecting unit 6, which occurs at an angle ($\theta o$) of regular reflection that is the same as the angle ($\theta i$) of incidence. This predetermined arrangement assures that, as can be seen from FIG. 1, the incident light Li is directed to the center point 3 of irradiation on the surface 1a of the paper 1 at which the center line of rotation referred to above lies, and a plane M of incidence and reflection through which the incident light Li and reflected light Lo pass is flush with the plane M of incidence and reflection before the sample table 2 is inclined at an angle (α) of inclination.

As illustrated in FIG. 1, the sample table 2 is designed such that it can be inclined at an angle (α) of inclination with a center axis defined by a line O of intersection of the plane M of incidence and reflection—through which the incident light Li and reflected light Lo pass—with the surface 1a of the paper 1 held on the support surface 2a of the sample table 2. If this angle (α) of inclination is within the range of 20° to 70°, preferably 40° to 70°, accurate data can then be obtained, as can be understood from the examples given later. Preferably, an angle control mechanism is provided so as to set that angle of inclination under free control within the angle range mentioned above.

Figure 2:
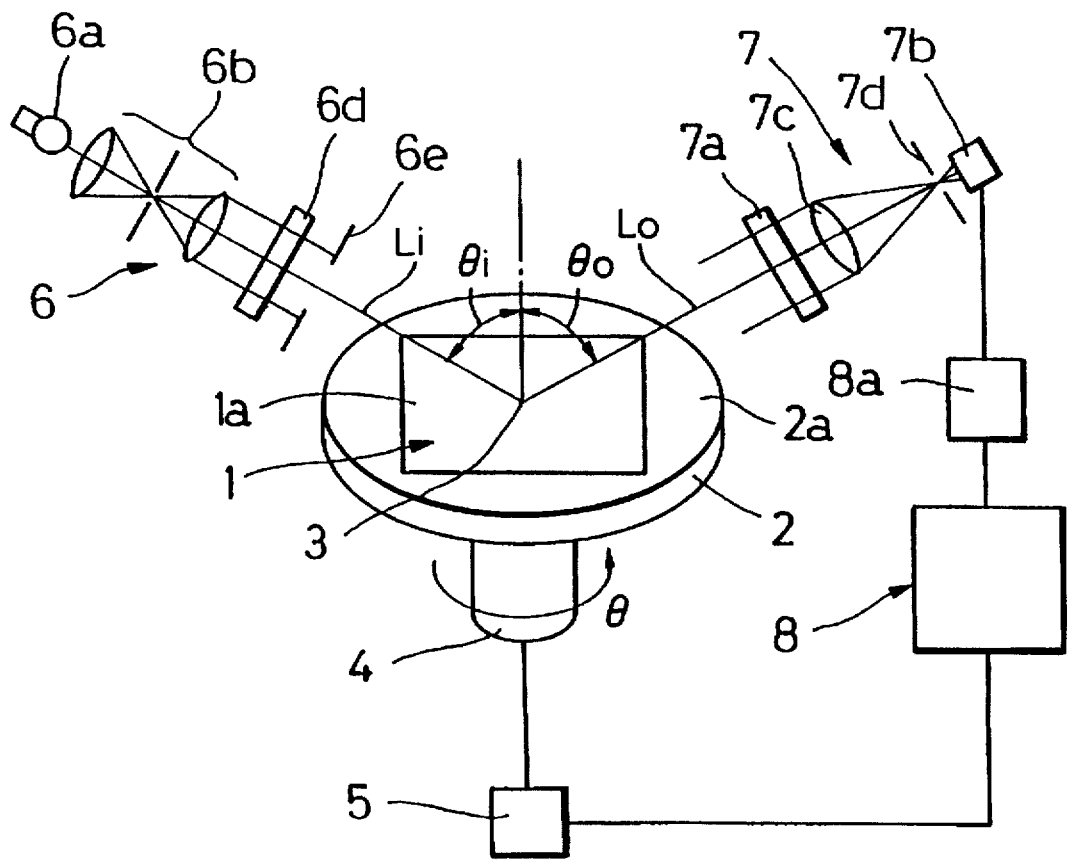
FIG. 2 is a schematic of one embodiment of the apparatus for carrying out the present method.
Figure 3:
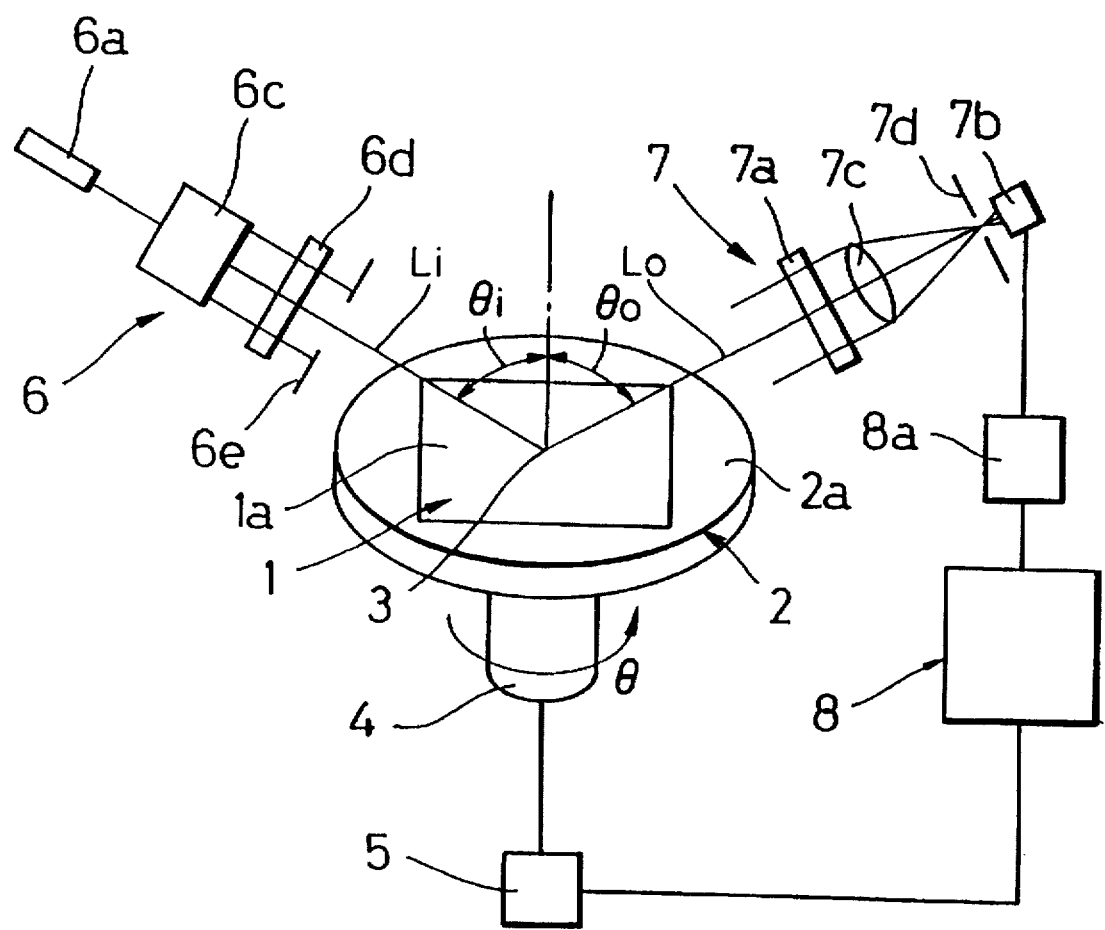
FIG. 3 is a schematic of another embodiment of the apparatus for practicing the present method.

The projecting unit 6 is built up of a light source 6a, a lens system 6b consisting of a lens for converging the light from the light source 6a so that parallel light can be directed to the surface 1a of the paper 1 when the light source 6a is an electric bulb such as an incandescent electric lamp or halogen lamp as typically shown in FIG. 2, a pinhole for converging the transmitted light and a lens for converting the light transmitted through the pinhole into parallel light, and a beam expander 6c for expanding the diameter of the light from the light source 6a when the light source 6a is a semiconductor laser or as a He-Ne laser as typically shown in FIG. 3. If required, there may additionally be provided a polarizer 6d for polarizing the light coming from the light source 6a into a linearly polarized principal ray or a diaphragm 6e of given diameter for directing a light beam of given diameter from the light source 6a to the surface 1a of the paper 1. Preferable as this diaphragm 6e is one that enables a light beam having a diameter of 20 mm or longer to be directed to the surface 1a of the paper 1 so as to find a mean value. This is because if the diameter of the light beam directed to the surface 1a of the paper 1 is smaller than 10 mm, local orientations are then more or less detected due to the texture of the paper 1 or for other reasons. Furthermore in this case, it is preferable that the diaphragm 6e becomes parallel with the surface 1a of the paper 1 when it is inclined at the angle (α) of inclination with respect to the center line O of intersection of the plane M of incidence and reflection through the incident light Li and reflected light Lo pass with the surface 1a of the paper 1 held on the support surface 2a of the sample table 2, so that the incident light Li is made to have a circular shape on the surface 1a of the paper 1.

As shown in FIGS. 2 and 3, the receiving unit 7 for receiving the reflected light Lo includes a polarizer 7a which is placed in a polarizer support base with a 90° rotation mechanism and in which at least the light ray received is converted into a linearly polarized principal ray alone or a linearly polarized ray having an oscillation parallel with the above-mentioned plane M of incidence and reflection (that will hereinafter be called the linearly polarized subordinate ray) and a photoelectric conversion element 7b. If required, it may further include a receiving lens 7c and a pinhole 7d for removal of stray light. The stray light-removing pinhole 7d is located at the focal position of the receiving lens 7c for concentrating the reflected light Lo reflected by and off the surface 1a of the paper 1 for removal of stray light such as intra-layer diffused ray. The photoelectric conversion element 7b used, for instance, may be a photomultiplier tube or photodiode designed to receive at least the linearly polarized principal ray alone as the reflected light Li reflected off the surface 1a of the paper 1 at the angle (θ) of regular reflection, thereby detecting the intensity thereof.

As noted earlier, the projecting and receiving units 6 and 7 are arranged such that the angle (θi) of incidence of the incident light Li and the angle (θo) of reflection of the reflected light Lo, both with respect to the line vertical to the line O of intersection of the plane M of incidence and reflection with the support surface 2a of the sample table 2, are equal to each other within the plane M of incidence and reflection. Referring here to the angle (θi) of incidence of the incident light Li and the angle (θo) of reflection of the reflected light Lo, it is not preferable that both are too large or too small. Too small angles result in an increase in the intra-layer diffused ray. Too large angles do not only incur increase in the size of a system size due to the need of making small the projecting unit and receiving units 6 and 7 or spacing them farther away from the sample table 2, but have also an adverse influence on the capacity of the photoelectric conversion element 7b of the receiving unit 7. Thus, an angle within the range of 30° to 80° is suitable for the measurement of fiber orientation. The preferable angle range lies at 50° to 70° at which precise data of high reproducibility can be obtained.

In the present invention, there is provided a computer 8 to which the intensity of the reflected light Lo amplified through an amplifier 8a which is to amplify the intensity of the reflected light Lo received by the photoelectric conversion element 7b of the receiving unit 7 is fed together with the then angle (θ) of rotation of the sample table 2. The signals fed into the computer 8 may be in an analog or digital form. By this computer 8 the relation between the intensity of the reflected light Lo received by the receiving unit 7 and the then angle (θ) of rotation of the sample table 2 is found in the form of a periodic function with a 360° period. For instance, the angle (θ) of rotation of the sample table 2 (the angle of fiber orientation) upon the intensity of the reflected light Lo received by the receiving unit 7 reaching a maximum, and the ratio of the intensity of the reflected light Lo received by the receiving unit 7 at the angle of fiber orientation to the intensity of the reflected light Lo by the receiving unit 7 in the direction normal to the angle of fiber orientation (the intensity of fiber orientation) can be found from the periodic function mentioned above.

To find the fiber orientation of the paper 1, e.g., the angle and intensity of fiber orientation according to the method of the present invention, the paper 1 to be measured is first supported on the support surface 2a of the sample table 2 as by use of an adhesive tape, while the machine direction is kept parallel with the line O of intersection of the paper surface 1a with the plane M of incidence and reflection through which the incident light Li and reflected light Lo pass. Then, it is ascertained whether or not the paper surface 1a is inclined at the angle (α) of inclination with respect to the center axis defined by the line O of the surface 1a of the paper 1 with the plane M of incidence and reflection through which the incident light Li coming from the projecting unit 6 and the reflected light Lo regularly reflected by the surface 1a of the paper 1 pass. Afterwards, the paper 1 is rotated relative to the plane M of incidence and reflection around the center axis of rotation defined by the line that passes through the center point 3 of the paper surface 1a which is irradiated with the incident light Li, and is vertical to the paper surface 1a (in the illustrated example the drive unit 4 is actuated to turn the sample table 2), so that the angle of turning of the paper 1 (in the illustrated example the angle detected by the rotary encoder 5) and the intensity of the reflected light Lo corresponding to that angle and received by the receiving unit 7 are successively fed into the computer 8, thereby finding the fiber orientation of the surface of the paper 1.

For determining the orientation of fibers according to the method of the present invention, it is an essential requirement that the incident light Li to be irradiated from the projecting unit 6 to the surface 1a of the paper 1 supported on the support surface 2a of the sample table 2 contain at least the linearly polarized principal ray and the reflected light Lo contain at least the linearly polarized principal ray alone. In the method of the present invention, however, the following three combinations of the incident light Li projected from the projecting unit 6 and the reflected light Lo received by the receiving unit 7 are possible.

(1) One combination comprises the incident light Li containing a natural ray of lights and the reflected light Lo containing the linearly polarized principal ray alone. In this combination, the natural light ray is used as the incident light Li or, to put it another way, the incident light Li contains the linearly polarized subordinate ray that passes readily through the cellulose fiber. Upon passing through the cellulose fiber, the linearly polarized subordinate ray then gives rise to the linearly polarized principal ray by the intra-layer diffusion. It is thus believed that the proportion of errors contained in the obtained measurements reaches a maximum in the method of the present invention.

(2) Another combination comprises the incident light Li containing the linearly polarized principal ray alone and the reflected light Lo containing the linearly polarized principal ray alone. In this combination, since the incident light Li does not contain the linearly polarized subordinate ray that passes readily through the cellulose fiber, the quantity of the ray passing through the cellulose fiber is small and hence the quantity of the intra-layer diffused ray is reduced; that is, the proportion of errors in data is smaller than that in the first combination mentioned just above. However, since a part of the linearly polarized principal ray used as the incident light Li passes through the cellulose fiber to introduce the intra-layer diffused ray, which has no specific oscillation direction, the linearly polarized principal ray contained in the intra-layer diffused ray, too, is received by the receiving unit in the form of the reflected light Lo. Thus it is believed that the obtained data still contain errors.

(3) Still another or the final combination comprises the incident light Li containing the linearly polarized principal ray alone and the reflected light Lo containing the linearly polarized subordinate ray in addition to the linearly polarized principal ray. The intensity of the reflected light Lo is then found by subtracting the intensity of the linearly polarized subordinate ray from the intensity of the linearly polarized principal ray received. In this combination, the incident light Li does not contain the linearly polarized subordinate ray that passes easily through the cellulose fiber, and the intensity of the intra-layer diffused ray having no specific oscillation direction due to the passage through the paper layer of part of the linearly polarized principal ray is the same when the linearly polarized principal and subordinate rays are separated and thus subtracted from the said combination (2). Thus it is believed that the obtained data contain the smallest errors. When the method of the present invention is practiced with this combination, the intensity of the reflected light Lo received by the receiving unit 7 corresponding to the angle of rotation of the same paper 1 (the angle detected by the rotary encoder 5 in the case of the illustrated example) must be defined by two intensities, i.e., that of the linearly polarized principal ray alone and that of the linearly polarized subordinate ray alone. These two rays may be received by the receiving unit in such a manner that the reception of the linearly polarized principal ray alone is followed by the reception of the linearly polarized subordinate ray alone for which the polarizer 7a is rotated by an angle of 90°. Alternatively, a half-mirror is located on the optic axis of the receiving unit 7 with a polarizer for the linearly polarized principal ray mounted on one half of the optic axis and a polarizer for the linearly polarized subordinate ray mounted on the other half of the optic axis, so that the two rays can be measured simultaneously.

EXAMPLES

Using an oriented sheet machine (available under the trade name of "ORIENTED SHEET FORMER", manufactured by Kumagaya Riki Kogyo Co., Ltd.), two paper sheets having a weight of 80 g/m$^2$, one of high surface fiber orientation and the other of low surface fiber orientation, were made at a varying pump pressure for feeding the raw material to the nozzle. The raw material used was L-BKP (with the degree of water filtration being 500 ml) blended with 5% of previously dyed cellulose fibers.

These two paper sheets were experimented with a direct method wherein how many fibers are present on a given area of surface of the paper at a given angle is calculated, a comparative method wherein unpolarized natural light rays are used for the incident light Li and reflected light Lo, and methods involving the above-mentioned combination (1) (Example 1), combination (2) (Example 2) and combination (3) (Example 3) to determine the angle and intensity of fiber orientation every 10° over the angle of inclination range of 0° to 70°.

The obtained data are reported in Tables 1 and 2 wherein the angle and intensity of fiber orientation on the surface of the paper having low fiber orientation are mentioned, respectively, and in Tables 3 and 4 wherein the angle and intensity of fiber orientation on the surface of the paper having high fiber orientation are mentioned, respectively.

TABLE 1

Data in Comparative Example and Examples on the angle of fiber orientation of paper sheets having low fiber orientation, the angle of fiber orientation of which is found to be 4.0 by the direct method

| Angle of Incination | Comparative Example | Example 1 | Example 2 | Example 3 |
|---|---|---|---|---|
| 0° | 86.7° | 25.2° | 80.6° | 89.6° |
| 10° | 9.5° | 5.1° | 2.5° | 2.7° |
| 20° | 5.1° | 3.5° | 3.0° | 4.0° |
| 30° | 3.6° | 3.9° | 3.5° | 3.8° |
| 40° | 3.9° | 4.0° | 3.8° | 4.1° |
| 50° | 4.2° | 4.0° | 4.1° | 4.3° |
| 60° | 4.7° | 3.0° | 4.3° | 4.0° |
| 70° | 4.3° | 4.0° | 4.1° | 4.0° |

TABLE 2

Data in Comparative Example and Examples on the intensity of fiber orientation of paper sheets having low fiber orientation, the intensity of fiber orientation of which is found to be 1,703 by the direct method

| Angle of Incination | Comparative Example | Example 1 | Example 2 | Example 3 |
|---|---|---|---|---|
| 0° | 1.014 | 1.010 | 1.014 | 1.051 |
| 10° | 1.079 | 1.105 | 1.116 | 1.144 |
| 20° | 1.121 | 1.146 | 1.179 | 1.291 |

TABLE 2-continued

Data in Comparative Example and Examples on the intensity of fiber orientation of paper sheets having low fiber orientation, the intensity of fiber orientation of which is found to be 1,703 by the direct method

| Angle of Incination | Comparative Example | Example 1 | Example 2 | Example 3 |
|---|---|---|---|---|
| 30° | 1.137 | 1.157 | 1.191 | 1.387 |
| 40° | 1.146 | 1.162 | 1.195 | 1.433 |
| 50° | 1.153 | 1.167 | 1.195 | 1.410 |
| 60° | 1.153 | 1.169 | 1.191 | 1.427 |
| 70° | 1.150 | 1.161 | 1.191 | 1.427 |

TABLE 3

Data in Comparative Example and Examples on the angle of fiber orientation of paper sheets having high fiber orientation, the angle of fiber orientation of which is found to be −2.0° by the direct method

| Angle of Incination | Comparative Example | Example 1 | Example 2 | Example 3 |
|---|---|---|---|---|
| 0° | −65.7° | −18.4° | −47.7° | −84.7° |
| 10° | −2.9° | −3.3° | −2.4° | −2.8° |
| 20° | −2.2° | −2.9° | −1.9° | −2.8° |
| 30° | −2.1° | −2.9° | −2.0° | −2.0° |
| 40° | −2.1° | −2.8° | −2.0° | −2.1° |
| 50° | −2.1° | −2.6° | −2.1° | −2.0° |
| 60° | −2.0° | −2.3° | −2.0° | −2.0° |
| 70° | −2.0° | −2.1° | −2.0° | −2.0° |

TABLE 4

Data in Comparative Example and Examples on the intensity of fiber orientation of paper sheets having high fiber orientation, the intensity of fiber orientation which is found to be 12.300 by the direct method

| Angle of Incination | Comparative Example | Example 1 | Example 2 | Example 3 |
|---|---|---|---|---|
| 0° | 1.020 | 1.039 | 1.014 | 1.051 |
| 10° | 1.179 | 1.281 | 1.323 | 1.433 |
| 20° | 1.326 | 1.445 | 1.587 | 2.165 |
| 30° | 1.398 | 1.500 | 1.685 | 3.065 |
| 40° | 1.448 | 1.535 | 1.729 | 4.063 |
| 50° | 1.491 | 1.571 | 1.755 | 4.128 |
| 60° | 1.545 | 1.584 | 1.751 | 4.128 |
| 70° | 1.540 | 1.580 | 1.750 | 4.128 |

INDUSTRIAL APPLICABILITY

Unlike the direct method mentioned above, the present method as explained in detail enables the orientation of fibers on the surface of paper to be readily determined with no need of the operator to use a magnifier or other means to separately count up the number of cellulose fibers for each angle of orientation. In addition, since the orientation of fibers on the surface of paper alone can be determined with no measurement of the orientation of fibers throughout the entire layer of paper which has been carried out so far in the art, it is possible to determine effectively and within a short time a measure of judging significant factors of paper depending on a fiber orientation difference between the two sides of paper, for instance, curling, warping, and twisting.

The obtained data are of so high precision that the orientation of fibers of the surface of paper can reliably be determined, partly because the intra-layer diffused ray is considerably or eliminated due to the design that at least the linearly polarized principal ray is received by the receiving unit, and partly because the light reflected by fibers lying parallel with the line of intersection of the plane of incidence and reflection with the surface of the paper is mainly received by the receiving unit due to the design that the surface of the paper is inclined at an angle of inclination with respect to the center axis defined by the line of the surface of the paper with the plane of incidence and reflection through which the incident light and reflected light pass.

Since, in the invented method, the paper to be measured is in no contact with a set of the projecting and receiving units, the data obtained about the orientation of fibers on the surface of the paper being made and processed can immediately be fed back modify the paper-making and process conditions by rotating the set of the projecting and receiving units relative to the inclined surface of the paper.

Furthermore, the invented method has a very wide range of applications, because it is applicable to the determination of the orientation of fibers not only on the surface of paper but also on the surfaces of various non-woven fabrics.

Thus the invented method has many technical merits and so makes a breakthrough in the art.

What is claimed is:

1. A method of determining the fiber orientation on the surface (1a) of paper (1) by directing incident light (Li) from a projecting unit (6) to the surface (1a) of the paper (1) to be measured at a given angle (θi) of incidence, and receiving by a receiving unit (7) the intensity of light (Lo) reflected by and off the surface (1a) of the paper (1) at the same angle (θo) of regular reflection as the angle (θi) of incidence, wherein:

the incident light (Li) containing at least a linearly polarized ray having an oscillation plane vertical to a plane (M) of incidence and reflection through which the incident light (Li) and reflected light (Lo) pass or a linearly polarized principal ray is allowed to be incident on the surface (1a) of the paper (1), so that at least the linearly polarized ray alone can be received by the receiving unit in the form of the reflected light (Lo), and the surface (1a) of the paper (1) is inclined at an angle (α) of inclination around a line (O) of intersection of the plane (M) of incidence and reflection through which the incident light (Li) and reflected light (Lo) pass with the surface (1a) of the paper (1) while the paper (1) is rotated relative to the plane (M) of incidence and reflection around a center axis of rotation defined by a line that passes through a center point (3) of the surface (1a) of the paper (1) irradiated with the incident light (Li) and is vertical to the surface (1a) of the paper (1), whereby the fiber orientation on the surface (1a) of the paper (1) can be found from the intensity of the reflected light (Lo) received by the receiving unit (7) corresponding to the angle of rotation of the paper (1).

2. The method of determining the orientation of fibers on the surface of paper according to claim 1, wherein the incident light (Li) used is natural ray of lights the receiving unit (7) receives the linearly polarized principal ray alone as the reflected light (Lo).

3. The method of determining the orientation of fibers on the surface of paper according to claim 1, wherein the incident light (Li) used is the linearly polarized principal ray alone and the receiving unit (7) receives the linearly polarized principal ray alone as the reflected light (Lo).

4. The method of determining the orientation of fibers on the surface of paper according to claim 1, wherein the incident light (Li) used is the linearly polarized principal ray, and the receiving unit (7) receives as the reflected light (Lo), in addition to the linearly polarized principal ray, a linearly polarized ray alone having an oscillation plane parallel with the plane (M) of incidence and reflection through which the incident light (Li) and reflected light (Lo) pass, or a linearly polarized subordinate ray alone, so that the intensity of the reflected light (Lo) can be found by subtracting the intensity of the linearly polarized subordinate ray from the intensity of the linearly polarized principal ray received.

5. The method of determining the orientation of fibers on the surface of paper according to any one of claims 1 to 4, wherein the angle ($\alpha$) of inclination lies in the range of 20° to 70°.

6. The method of determining the orientation of fibers on the surface of paper according to any one of claims 1 to 4, wherein the angle ($\theta$) of incidence of the incident light (Li) lies in the range of 30° to 80°.

7. A method of determining the orientation of fibers on a surface of paper, comprising the steps of:

projecting incident light onto the surface so that the incident light is reflected to produce reflected light, the incident and reflected light defining a plane M;

linearly polarizing at least a portion of the incident light in an oscillation plane perpendicular to the plane M, thereby forming a principal ray;

inclining the surface at an angle of inclination $\alpha$ about a line O defined by the intersection of the surface with the plane M;

rotating the surface about an axis intersecting the line O;

measuring the intensity of at least a portion of the reflected light; and determining the fiber orientation based upon the measured intensity.

8. The method of claim 7 wherein all of the incident light is polarized in an oscillation plane perpendicular to the plane M, thereby forming the principal ray.

9. The method of claim 7 including the step of polarizing a part of the reflected light in an oscillation plane parallel to the plane M, thereby forming a subordinate ray.

10. The method of claim 9 wherein said measuring step comprises measuring both said principal ray and said subordinate ray.

11. The method of claim 10 wherein said determining step comprises subtracting the subordinate ray from the principal ray.

12. The method of claim 7 wherein $\alpha$ is between 20° and 70°.

13. The method of claim 7 wherein an angle of incidence of the incident light is between 30° and 80°.

14. A method of determining the orientation of fibers on a surface of paper, comprising the steps of:

projecting incident light onto the surface so that the incident light is reflected to produce reflected light, the incident and reflected light defining a plane M, at least a portion of the incident light being oriented in an oscillation plane perpendicular to the plane M, thereby forming a principal ray;

inclining the surface at an angle of inclination $\alpha$ about a line O defined by the intersection of the surface with the plane M;

rotating the surface about an axis intersecting the line O;

measuring only the intensity of the principal ray; and determining the fiber orientation based upon the measured intensity.

* * * * *